United States Patent [19]

Stähler

[11] 4,322,371
[45] Mar. 30, 1982

[54] PROCESS FOR THE MANUFACTURE OF 2-CHLOROETHANE-PHOSPHONIC ACID

[75] Inventor: Gerhard Stähler, Frankfurt am Main, Fed. Rep. of Germany

[73] Assignee: Hoechst Aktiengesellschaft, Frankfurt am Main, Fed. Rep. of Germany

[21] Appl. No.: 871,550

[22] Filed: Jan. 23, 1978

Related U.S. Application Data

[63] Continuation of Ser. No. 701,184, Jun. 30, 1976, abandoned, which is a continuation of Ser. No. 207,619, Dec. 13, 1971, abandoned.

[30] Foreign Application Priority Data

Dec. 15, 1970 [DE] Fed. Rep. of Germany ....... 2061610
Sep. 29, 1971 [DE] Fed. Rep. of Germany ....... 2148549

[51] Int. Cl.$^3$ ............................................. C07F 9/38
[52] U.S. Cl. ............................................ 260/502.4 R
[58] Field of Search ................................. 260/502.4 R

[56] References Cited

FOREIGN PATENT DOCUMENTS 1565742 3/1959 France ...................... 260/502.4 R

OTHER PUBLICATIONS

Kabachnik et al., "Chem. Abstracts", vol. 42 (1948), cols. 7241-7243.
Luder et al., "General Chemistry", 2nd Ed. (1959), pp. 169-182.
Lange, "Handbook of Chemistry", 10th Ed. (1961) pp. 1468-1469.

*Primary Examiner*—Joseph E. Evans
*Attorney, Agent, or Firm*—Curtis, Morris & Safford

[57] ABSTRACT

An improved process for the manufacture of 2-chloroethane-phosphonic acid in which 2-chloroethane-phosphonic acid bis(2-chloroethyl) ester is heated with 50 to 500% by weight of aqueous hydrochloric acid at temperatures above 100° C. under pressure, the 1,2-dichloroethane formed during the reaction is continuously or discontinuously distilled off and the decrease in pressure is compensated by adding gaseous hydrogen chloride.

6 Claims, No Drawings

PROCESS FOR THE MANUFACTURE OF 2-CHLOROETHANE-PHOSPHONIC ACID

This is a continuation of application Ser. No. 701,184 filed June 30, 1976, now abandoned, which is in turn a continuation of application Ser. No. 207,619 filed Dec. 13, 1971, now abandoned.

The present invention relates to a process for the manufacture of 2-chloroethane-phosphonic acid.

2-Chloroethane-phosphonic acid is of industrial importance as ripening promotor and growth regulator as well as intermediate for the manufacture of polyvinyl-phosphonic acid used in corrosion protection.

Processes for the manufacture of 2-chloroethane-phosphonic acid and its precursors have been described in German Pat. No. 1,123,667 and French Pat. No. 1,558,691; furthermore by Kabachnik et al. (Chem. Abstr. 42, 7241-43), French Pat. No. 1,565,742 and German Application No. 1,815,999 laid open to public inspection.

The most economic process from among the three former publications appears to be the three step process disclosed by Kabachnik et al. and carried out according to the following scheme:

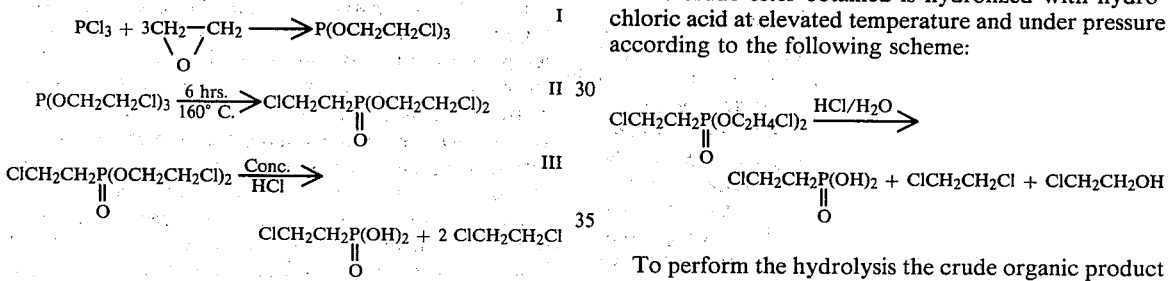

owing to the fact that the starting products phosphorus trichloride and ethylene oxide are cheap industrial products. However, according to Kabachnik, of a non-distillable residue 10 to 20% are formed in the first step and more than 50% in the second step. Although this amount of residue could be reduced by carrying out the reactions in suitable solvents this would require in both steps costly distillations under strongly reduced pressure and at elevated temperature. In the third step Kabachnik et al. describe the hydrolysis of the pure 2-chloroethane-phosphonic acid bis-(2chloroethyl) ester by means of concentrated hydrochloric acid but with partial success only. The reaction product must therefore be subjected, after distillation of the excess hydrochloric acid, to further purification operations to obtain a product of satisfactory purity.

In further developing the aforesaid process French Pat. No. 1,565,742 describes the rearrangement of tris-(2-chloroethyl)- phosphite in high boiling solvents, for example o-dichlorobenzene, cumene or xylene, at 150 to 160° C. The phosphonate obtained is hydrolized, without further purification, with gaseous hydrogen chloride or 20% aqueous hydrochloric acid. The product obtained with gaseous hydrogen chloride according to Example 1 of that patent contains about 30% of 2-chloro-ethane-phosphonic acid anhydride as a by-product besides 2-chloroethane-phosphonic acid as is evidenced by Example 1 of German Pat. No. 1,815,999 cited above and describing exactly the same procedure. The reproduction of Example 2 yielded 112% of the weight to be expected of a non-crystallizing colorless oil containing, according to the analysis, 0.5% of 2-chloroethane-phosphonic acid bis-(2-chloroethyl) ester, 8% of 2-chloroethane phosphonic acid mono-(2-chloroethyl) ester, 40% of 2-chloroethane -phosphonic acid, and 8-9% of 2-hydroxy-ethane-phosphonic acid. According to Tetrahedron Letters 15, pages 1281-1284 the latter is formed in a secondary reaction when 2-chloroethane-phosphonic acid is heated with 20% hydrochloric acid. The remainder which could not be determined by the analysis must be considered as partially dissociated polycondensate.

The present invention provides a process for the manufacture of 2-chloroethane-phosphonic acid by cleavage of 2-chloroethane-phosphonic acid bis(2-chloroethyl) ester which comprises carrying out the cleavage with 50 to 500% by weight of aqueous hydrochloric acid, at a temperature above 100° C. under elevated pressure, distilling off the 1,2-dichloroethane formed during the reaction either continuously or discontinuously, and compensating the fall in pressure during the reaction by adding gaseous hydrogen chloride. When operating in this manner 2-chloroethane-phosphonic acid is obtained in good yield and with good purity.

The crude ester obtained is hydrolized with hydrochloric acid at elevated temperature and under pressure according to the following scheme:

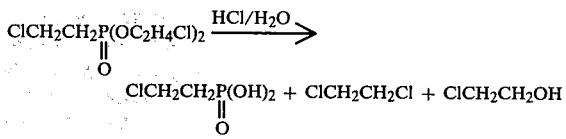

To perform the hydrolysis the crude organic product is heated at a temperature above 100° C., preferably above 120° C., while stirring in an autoclave made of a material that is resistant to hydrochloric acid, with 50 to 500% by weight, advantageously 100 to 300% by weight, calculated on the basis of the crude chloroethane-phosphonic acid bis(2-chloroethyl) ester, of hydrochloric acid having a strength of preferably 30 to 38%. With increasing temperature the purity of the final product gradually decreases so that it is not advisable to operate at temperature above 200° C. In the reaction vessel a pressure in the range of from 1 to 10 atmospheres gauge, preferably 3 to 6 atmospheres gauge, is maintained, if necessary by forcing in hydrogen chloride. The dichloroethane formed is repeatedly distilled off by releasing the overpressure. The escaping hydrogen chloride and the hydrogen chloride used up by the reaction are replenished by forcing in again hydrogen chloride. When the reaction vessel in connected with a collecting vessel by means of a closed reflux condenser the dichloroethane can be removed continuously, whereby losses of hydrogen chloride are avoided.

At a temperature of 130° C., for example, the hydrolysis is terminated after approximately 4 hours. The aqueous hydrochloric acid which still contains small amounts of 2-chloroethanol is distilled off at 20°-100° C. under reduced pressure.

In the process according to the present invention the desired 2-chloroethane-phosphonic acid is obtained practically pure and with excellent yields. The reaction can be performed with pure starting compound as well as with a non-purified product as obtained by the reaction of ethylene oxide with phosphorus trichloride with subsequent rearrangement of the tris(2-chloroethyl)-phosphite formed to the corresponding phosphonate.

The following Examples illustrate the invention.

EXAMPLE 1

(a) Preparation of 2-chloroethane-phosphonic acid bis(2-chloroethyl) ester

The reaction was carried out in a 2 liter flask provided with stirrer, thermometer and reflux condenser the outlet of which was closed by a pressure compensating vessel containing as sealing liquid o-dichlorobenzene saturated with ethylene oxide and which contained a mixture of 500 grams of phosphorus trichloride and 500 grams of o-dichlorobenzene. The apparatus was scavenged with nitrogen and, while stirring and cooling at 20°–30° C., 500 grams of ethylene oxide were introduced into the mixture at a rate such that the ethylene oxide was fully absorbed. The introduction of ethylene oxide was continued for 3 to 4 hours while cooling with ice. The reaction mixture was allowed to stand for 6 hours at room temperature and then heated for 8 hours at 160° C. The o-dichlorobenzene was distilled off at 2 to 20 Torr leaving a residue of 855 grams of crude 2-chloroethane-phosphonic acid bis(2-chloroethyl) ester.

(b) Hydrolysis of the crude 2-chloroethane-phosphonic acid bis(2-chloroethyl) ester In an enamelled autoclave provided with stirrer and having a capacity of at least 2.5 liters the product of (a) was heated for 2 hours at 120° C. together with 850 grams of concentrated hydrochloric acid. During heating the pressure rose to about 4 atmospheres gauge. The pressure of the autoclave was released over a condenser and the 1,2-dichloroethane formed was thus distilled off. The temperature of the reaction mixture dropped to 95° C. Through an inlet in the cover of the autoclave (no ascending tube) hydrogen chloride from a bomb was forced in to increase the pressure again to 3 atmospheres gauge. The temperature rose to 130° C. and was maintained at 130°–140° C. for 2 hours by heating. The pressure of the autoclave was then released again over the condenser whereby another 430 grams of 1,2-dichloroethane were obtained. The aqueous hydrochloric acid was distilled off at an internal temperature of 100° C., first at 30 to 70 Torr finally at 2 Torr. 450–470 Grams of 2-chloroethane-phosphonic acid having a solidification point of 62°–66° C. and a purity of 94–98% were obtained (about 90% of the theory over all three steps, calculated on the amount of phosphorus trichloride used).

EXAMPLE 2

An enamelled steel vessel having a capacity of 150 liters nd provided with heating jacket, stirrer, thermometer and a descending condenser connected via a valve was filled with a mixture of 30 kilograms of phosphorus trichloride and 30 kilograms of o-dichlorobenzene. It was then scavenged with nitrogen and, while stirring and cooling at 20–35° C., 30 kilograms of ethylene oxide were introduced during the course of 3 to 5 hours at a rate such that the ethylene oxide was completely absorbed. Stirring of the reaction mixture was continued for 6 hours at room temperature, then the mixture was heated for 8 hours at 150°–170° C. and the o-dichlorobenzene was distilled off at 2 to 20 Torr.

After adding 60 kilograms of concentrated hydrochloric acid the connection of the reaction vessel to the descending condenser and all other openings of the vessel were closed. The reaction mixture was heated to 130° C. during the course of 1 hour whereby the internal pressure rose to 5 atmospheres gauge. The overpressure was released by opening the valve to the condenser. The 1,2-dichloroethane formed distilled off while the content of the vessel cooled to 100° C.

The internal pressure of the reaction vessel was increased to 3 atmospheres gauge by forcing in gaseous hydrogen chloride from a steel cylinder whereby the internal temperature rose to 130° C. This operation was repeated twice at intervals of one hour. A total amount of 15 to 16 kilograms of 1,2-dichloroethane was distilled off. After the last repetition the reaction mixture was heated at 130°–140° C. for another hour, the pressure of the vessel was released and aqueous hydrochloric acid and a small amount of 2-chloroethanol were distilled off at an internal temperature of 100° C., first at 40 and finally at 2 to 5 Torr.

28 to 29 Kilograms of 2-chloroethane phosphonic acid having a solidification point of 63°–64° C. and a purity of 95% were obtained, the overall yield being 92% of the theory.

EXAMPLE 3

100 Kilograms of crude 2-chloroethane-phosphonic acid bis(2-chloroethyl) ester and 5 kilograms of concentrated hydrochloric acid were heated at the reaction temperature while stirring in an 150 liter enamel-lined autoclave connected with an enamel-lined reflux condenser which in turn was connected with a collecting vessel via a cock. While distilling off the dichloroethane formed a HCl overpressure was produced by supplying hydrogen chloride and maintained until the formation of dichloroethane was terminated. The reaction mixture was heated at the reaction temperature for a further 3 hours, then the heating of the autoclave was switched off, the excess amount of hydrogen chloride was removed and the water contained in the reaction mixture was distilled off under reduced pressure. Finally, the residual amount of hydrogen chloride still present in the reaction mixture was removed by passing through nitrogen for one hour.

The following table summarizes reaction periods, consumption of hydrogen chloride, yields and purity of the reaction products obtained in a series of experiments carried out with a starting material containing 62% of 2-chloroethanephosphonic acid bis(2-chloroethyl) ester at different temperatures.

TABLE

| Temp. 0° C. | period hrs. | HCl consumption kg | yield kg | purity of 2-chloro-ethane-phosphonic acid % |
|---|---|---|---|---|
| 160 | 20 | 34 | 55.5 | 96 |
| 170 | 15 | 35 | 53.5 | 94 |
| 180 | 14 | 36 | 53 | 91 |
| 190 | 13 | 34 | 53 | 90 |

What is claimed is:

1. In a process for the manufacture of 2-chloroethanephosphonic acid by the hydrolytic cleavage of 2-chloroethanephosphonic acid bis(2-chloroethyl) ester, the improvement which comprises contacting said ester with 50 to 500 percent of concentrated, 30–38 percent, aqueous hydrochloric acid, by weight of said ester, at a temperature above 100° C. and under an elevated pressure, distilling off the 1,2-dichloroethane formed during the reaction, and maintaining an elevated pressure during the reaction by adding gaseous hydrogen chloride.

2. The process as in claim 1, wherein 1,2-chloroethane is distilled off discontinuously.

3. The process in claim 1, wherein 1,2-dichloroethane is distilled off continuously.

4. The process of claim 1, wherein a pressure of from 1 to 10 atmospheres gauge is maintained during hydrolysis.

5. The process of claim 4, wherein the pressure is 3 to 6 atmospheres gauge.

6. The process of claim 1, wherein the hydrolysis is carried out at a temperature of from 110° to 190° C.

* * * * *